United States Patent
Chen et al.

(10) Patent No.: US 11,350,895 B2
(45) Date of Patent: Jun. 7, 2022

(54) SYSTEM AND METHOD FOR SPECTRAL COMPUTED TOMOGRAPHY USING SINGLE POLYCHROMATIC X-RAY SPECTRUM ACQUISITION

(71) Applicant: Wisconsin Alumni Research Foundation, Madison, WI (US)

(72) Inventors: Guang-Hong Chen, Madison, WI (US); Yinsheng Li, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 356 days.

(21) Appl. No.: 16/699,222

(22) Filed: Nov. 29, 2019

(65) Prior Publication Data
US 2021/0161487 A1    Jun. 3, 2021

(51) Int. Cl.
*G01N 23/00* (2006.01)
*A61B 6/00* (2006.01)
(Continued)

(52) U.S. Cl.
CPC ............ *A61B 6/4241* (2013.01); *A61B 6/032* (2013.01); *G01T 1/36* (2013.01); *G06N 3/084* (2013.01);
(Continued)

(58) Field of Classification Search
CPC ....... A61B 6/5241; A61B 6/032; A61B 6/482; A61B 6/405; A61B 6/5205; A61B 5/4869; A61B 6/4035; A61B 6/4042; A61B 6/4241; A61B 6/06; A61B 6/4007; A61B 6/4411; A61B 6/4078; A61B 6/4275; A61B 6/5282; A61B 6/5264; A61B 6/4014; A61B 6/4476; A61B 6/4452; A61B 6/4405; A61B 6/0407; A61B 6/4266; A61B 6/5258; A61B 6/5217; A61B 6/4233; A61B 6/541; A61B 6/54; A61B 6/488; A61B 6/502; A61B 6/025; A61B 6/582; A61B 6/4208; A61B 8/587; A61B 5/004; A61B 5/1076; A61B 6/583; A61B 6/481; A61B 6/037;
(Continued)

(56) References Cited

U.S. PATENT DOCUMENTS

| | | | |
|---|---|---|---|
| 2009/0052621 A1* | 2/2009 | Walter | A61B 6/4035 378/53 |
| 2011/0052022 A1* | 3/2011 | Xu | G06T 11/005 382/131 |

(Continued)

OTHER PUBLICATIONS

Almeida IP, et al. Dual-energy CT quantitative imaging: a comparison study between twin-beam and dual-source CT scanners. Medical physics. 2017;44(1):171-9.
(Continued)

*Primary Examiner* — Irakli Kiknadze
(74) *Attorney, Agent, or Firm* — Quarles & Brady LLP

(57) ABSTRACT

A system and method for material decomposition of a single energy spectrum x-ray dataset includes accessing the single energy spectrum x-ray dataset, receiving a user-selection of a desired energy for decomposition, and decomposing the single energy spectrum x-ray dataset into material bases as a linear combination of energy dependence function of selected basis materials and the corresponding spatial dependence material bases images.

28 Claims, 7 Drawing Sheets

(51) Int. Cl.
  *A61B 6/03* (2006.01)
  *G01T 1/36* (2006.01)
  *G06T 11/00* (2006.01)
  *G06T 7/00* (2017.01)
  *G06N 3/08* (2006.01)

(52) U.S. Cl.
  CPC .......... *G06T 7/0012* (2013.01); *G06T 11/006* (2013.01); *G06T 2207/10072* (2013.01); *G06T 2207/30004* (2013.01)

(58) Field of Classification Search
  CPC ..... A61B 5/055; A61B 5/0075; A61B 5/7267; A61B 6/504; A61B 8/14; A61B 5/7475; A61B 5/742; A61B 8/12; A61B 5/0066; A61B 6/483; A61B 6/486; A61B 6/4085; A61B 6/4071; A61B 8/5223; A61B 5/02007; A61B 6/4291; A61B 6/4021; A61B 6/469; A61B 6/03; A61B 6/484; A61B 6/027; A61B 6/461; A61B 6/52; A61B 6/465; A61B 6/467; G06T 11/008; G06T 11/003; G06T 11/005; G06T 7/0012; G06T 11/006; G06T 7/20; G06T 5/001; G06T 5/50; G06T 2207/10072; G06T 2207/30004; G06T 5/002; G06T 2211/408; G06T 2211/40; G06T 2207/30048; G06T 2207/10101; G06T 2207/10104; G06T 2207/10108; G06T 2207/10132; G06T 2207/10081; G06T 2207/10116; G06T 2207/10088; G06T 2207/20101; G06T 2207/20081; G06T 2207/30101; G06T 7/60; G06T 2201/10116; G06T 2207/30068; G06T 2207/3024; G06T 2207/30242; G01N 23/046; G01N 23/087; G01N 23/20; G01N 23/044; G01N 2223/3301; G01N 2223/303; G01N 2223/401; G01N 2223/332; G01T 1/36; G01T 1/171; G01T 1/1663; G01T 1/366; G01T 1/249; G06N 3/084; G06N 20/00; G06N 3/0454; G06N 7/005; H04N 5/32; G06V 2201/03; G06V 10/247; G06V 10/42; G06V 10/462; G06K 9/6201; G06K 9/6298; G06K 9/627; A61K 49/04; A61K 49/0409
  USPC ....................... 378/4, 5, 53, 62, 19
  See application file for complete search history.

(56) References Cited

U.S. PATENT DOCUMENTS

| | | | |
|---|---|---|---|
| 2017/0278278 A1* | 9/2017 | Brown | G01N 23/046 |
| 2019/0167218 A1* | 6/2019 | Hsieh | A61B 6/405 |
| 2020/0196972 A1* | 6/2020 | Zhou | G06T 5/50 |
| 2021/0007691 A1* | 1/2021 | Prabhu Verleker | A61B 6/06 |

OTHER PUBLICATIONS

Alvarez RE, et al. Energy-selective reconstructions in x-ray computerised tomography. Physics in Medicine & Biology. 1976;21(5):733.
Cybenko G et al. Approximation by superpositions of a sigmoidal function. Mathematics of Control, Signals and Systems 2, 303-314 (1989).
De Man, B., et al. "An iterative maximum-likelihood polychromatic algorithm for CT." IEEE transactions on medical imaging 20.10 (2001): 999-1008.
Elbakri, I. A., et al. "Segmentation-free statistical image reconstruction for polyenergetic x-ray computed tomography with experimental validation." Physics in Medicine & Biology 48-15 (2003): 2453.
Elbakri, I. A., et al. "Statistical image reconstruction for polyenergetic X-ray computed tomography." IEEE transactions on medical imaging 21.2 (2002): 89-99.
Flohr TG, et al. First performance evaluation of a dual-source CT (DSCT) system. Eur Radiol. 2006;16(2):256-68.
Ghahramani Z. Probabilistic machine learning and artificial intelligence. Nature. 2015;521:452.
Hornik K., Approximation capabilities of multilayer feedforward networks. Neural Networks 4, 251-257, (1991).
Ko JP, et al. Dual-energy computed tomography: concepts, performance, and thoracic applications. Journal of thoracic imaging. 2012;27(1):7-22.
Lecun Y, et al. Deep learning. Nature. 2015;521(7553):436-44.
Lin XZ, et al. High-definition CT Gemstone spectral imaging of the brain: initial results of selecting optimal monochromatic image for beam-hardening artifacts and image noise reduction. Journal of computer assisted tomography. 2011;35(2):294-7.
Rumelhart DE, et al. Learning representations by back-propagating errors. Nature. 1986;323(6088):533-6.
Shikhaliev PM, et al. Photon counting computed tomography: concept and initial results. Medical physics. 2005;32(2):427-36.
Yu L, et al. Dual-energy CT-based monochromatic imaging. American journal of Roentgenology. 2012; 199(5_supplement):S9-S15.
Leng S, et al. Photon-counting Detector CT: System Design and Clinical Applications of an Emerging Technology. RadioGraphics. 2019;39(3):729-43.
Macovski A, et al. Energy dependent reconstruction in X-ray computerized tomography. Computers in biology and medicine. 1976;6(4):325-36.
Rutt B, et al. Split-filter computed tomography: a simple technique for dual energy scanning. Journal of computer assisted tomography. 1980;4(4):501-9.

\* cited by examiner

SYSTEM AND METHOD FOR SPECTRAL COMPUTED TOMOGRAPHY USING SINGLE POLYCHROMATIC X-RAY SPECTRUM ACQUISITION

STATEMENT REGARDING FEDERALLY SPONSORED RESEARCH

This invention was made with government support under EB021183 awarded by the National Institutes of Health. The government has certain rights in the invention.

CROSS-REFERENCE TO RELATED APPLICATIONS

N/A

BACKGROUND

The present disclosure relates to systems and methods for medical image data preparation, acquisition, and/or reconstruction. More particularly, systems and method are provided for generating spectrally-resolved images from single polychromatic x-ray spectrum computed tomography (CT) data.

In traditional computed tomography systems, an x-ray source projects a beam that is collimated to lie within an X-Y plane of a Cartesian coordinate system, termed the "imaging plane." The x-ray beam passes through the object being imaged, such as a medical patient, and impinges upon an array of radiation detectors. The intensity of the radiation received by each detector element is dependent upon the attenuation of the x-ray beam by the object and each detector element produces a separate electrical signal that relates to the attenuation of the beam. The linear attenuation coefficient is the parameter that describes how the intensity of the x-rays changes when passing through an object. Often, the "mass attenuation coefficient" is utilized because it factors out the dependence of x-ray attenuations on the density of the material. The attenuation measurements from all the detectors are acquired to produce the transmission map of the object.

The source and detector array in a conventional CT system are rotated on a gantry within the imaging plane and around the object so that the projection angle at which the x-ray beam intersects the object constantly changes. A group of x-ray attenuation measurements from the detector array at a given angle is referred to as a "view" and a "scan" of the object. These views are collected to form a set of views made at different angular orientations during one or several revolutions of the x-ray source and detector. In a two dimensional (2D) scan, data are processed to construct an image that corresponds to a 2D slice taken through the object. The prevailing method for reconstructing an image from 2D data is referred to in the art as the filtered backprojection (FBP) technique. This process converts the attenuation measurements from a scan into integers called "CT numbers" or "Hounsfield units", which are used to control the brightness of a corresponding pixel on a display.

The term "generation" is used in CT to describe successively commercially available types of CT systems utilizing different modes of scanning motion and x-ray detection. More specifically, each generation is characterized by a particular geometry of scanning motion, scanning time, shape of the x-ray beam, and detector system.

The first generation utilized a single pencil x-ray beam and a single scintillation crystal-photomultiplier tube detector for each tomographic slice. The second generation of CT systems was developed to shorten the scanning times by gathering data more quickly. In these units a fan beam is utilized, which may include anywhere from three to 52 individual collimated x-ray beams and an equal number of detectors.

To obtain even faster scanning times it is necessary to eliminate the complex translational-rotational motion of the first two generations. Third generation scanners therefore use a much wider, "divergent" fan beam. In fact, the angle of the beam may be wide enough to encompass most or all of an entire patient section without the need for a linear translation of the x-ray tube and detectors. As in the first two generations, the detectors, now in the form of a large array, are rigidly aligned relative to the x-ray beam, and there are no translational motions at all. The tube and detector array are synchronously rotated about the patient through an angle of 180-360 degrees. Thus, there is only one type of motion, allowing a much faster scanning time to be achieved. After one rotation, a single tomographic section is obtained.

Fourth generation scanners also feature a divergent fan beam similar to the third generation CT system. However, unlike in the other scanners, the detectors are not aligned rigidly relative to the x-ray beam. In this system only the x-ray tube rotates. A large ring of detectors are fixed in an outer circle in the scanning plane. The necessity of rotating only the tube, but not the detectors, allows faster scan time. Each x-ray projection view becomes a cone-beam shape instead of a fan-beam shape.

In addition to this "generational" evolution, dual-energy x-ray imaging systems have been created to acquire images of the subject at two different x-ray energy spectra. This can be achieved with a conventional third or fourth generation CT system by alternately acquiring views using two different x-ray tube anode voltages. Alternatively, two separate x-ray sources with associated detector arrays may be operated simultaneously during a scan at two different x-ray energy spectra. In either case, two registered images of the subject are acquired at two prescribed energy spectra. As will be described, multi-energy acquisitions are clinically advantageous because it allows for resolution of spectral information and material decomposition. Unfortunately, it also subjects the patient to an appreciably increased radiation dose, which is clinically undesirable and substantially limits the viability of acquiring the information, even beyond the substantial cost of the hardware needed to acquire such data.

The measurement of an x-ray transmission map attenuated by a subject at two distinct energy bands is often used to determine material-specific information of an imaged subject. This is based upon that fact that, in general, attenuation is a function of x-ray energy according to two attenuation mechanisms: photoelectric absorption and Compton scattering. These two mechanisms differ among materials of different atomic numbers. For this reason, measurements at two energies can be used to distinguish between two different basis materials. Dual energy x-ray techniques can be used, for example, to separate bony tissue from soft tissue in medical imaging, to quantitatively measure bone density, to remove plaque from vascular images, and to distinguish between different types of kidney stones.

To determine the effective atomic number and density of a material, the linear attenuation coefficient of the material, μ(r,E), can be expressed as a linear combination of the mass attenuation coefficients of two so-called basis materials, as follows:

$$\mu(r, E) = \left(\frac{\mu}{\rho}\right)_1 (E) \cdot \rho_1(r) + \left(\frac{\mu}{\rho}\right)_2 (E) \cdot \rho_2(r); \quad (1)$$

where r is the spatial location at which a measurement is made, E is the energy at which a measurement is made, $\rho_i(r)$ is the decomposition coefficient of the $i^{th}$ basis material, and $$\left(\frac{\mu}{\rho}\right)_i (E)$$

is the mass attenuation coefficient of the $i^{th}$ basis material. Thus, this method is commonly referred to as the basis-material method. In this method, CT measurements must be acquired using at least two energy levels (high and low) to solve the two unknowns $\rho_1(r)$ and $\rho_2(r)$. However, in practice, the detected signals comprised of a weighted summation over a wide range of x-ray energies due to the use of polychromatic x-ray sources in data acquisitions. The detected signals can be expressed as:

$$I_k = \int S_k(E) \cdot D(E) \cdot E \cdot e^{-\left[\left(\frac{\mu}{\rho}\right)_1 (E) \cdot L_1 + \left(\frac{\mu}{\rho}\right)_2 (E) \cdot L_2\right]} dE; \quad (2)$$

where $S_k(E)$ is the x-ray spectrum which accounts for the number of x-ray photons for the $k^{th}$ x-ray energy, D(E) is the detector energy response, $L_1 = \int dl \cdot \rho_1(r)$, and $L_2 = \int dl \cdot \rho_2(r)$, which represent the line integral of the densities of the two basis materials, respectively.

Accordingly, the basis-material method is a practical method to employ in a clinical setting when using dual-energy spectral CT. The decomposition coefficients, $\rho_i(r)$, can be interpreted as components in a two-dimensional vector space, with the basis materials defining the basis vectors. Fundamentally, decomposition and the creation of spectral information requires at least two data sets acquired using at least two distinct energies. This constraint severely limits clinical availability of spectrally-resolved CT data because one must have access to the specialized hardware and software required to acquire the multiple, registered datasets and because the patient must be subjected to additional radiation doses.

Thus, it would be desirable to have systems and methods that provide the ability to perform material decomposition without the drawbacks of needing to purchase specialized hardware and subjecting the patient to extra doses of radiation.

SUMMARY

The present disclosure provides systems and methods that allow material decomposition using one, single polychromatic x-ray spectrum CT acquisition, thereby avoiding additional radiation doses for the patient or the need for specialized hardware. In particular, the systems and methods provided herein allow for basis material analysis from a single polychromatic x-ray spectral CT dataset.

In accordance with one aspect of the disclosure, system is provided for performing material decomposition using a single spectrum x-ray dataset. The system includes a material basis generator configured to decompose the single spectrum CT dataset into at least two material basis images, an en-chroma generator configured to regularize the material basis generator by enforcing an effective energy constraint, and a sinogram generator configured to generate projection data for the at least two material basis images.

In accordance with another aspect of the disclosure, a method is provided for performing a material decomposition using a single polychromatic spectrum x-ray CT dataset. The method includes accessing the single spectrum x-ray dataset and decomposing the single spectrum x-ray dataset into a linear combination of energy dependence function, $b_k(\varepsilon)$, and corresponding expansion coefficients, $a_k(\vec{x})$, wherein $\vec{x}$ is a selected spatial location in the single-energy x-ray dataset, $\varepsilon$ is an x-ray energy in the single spectrum x-ray dataset at the selected spatial location, and k=1, 2, ..., K, to an index that labels material basis that is selected for decomposition and wherein $a_k(\vec{x}) = \Sigma_j a_{k,j} e_j(\vec{x})$, $e_j(\vec{x})$ is an expanded image voxel basis function, where $j \in [1,N]$ and $N = N_x N_y N_z$ is a total number of image voxels in an image formed from the single-energy x-ray dataset.

In accordance with one other aspect of the disclosure, a method is provided for performing a material decomposition of a single energy spectrum x-ray dataset. The method includes accessing the single energy spectrum x-ray dataset, receiving a user-selection of a desired energy for decomposition, and decomposing the single energy spectrum x-ray dataset into a linear combination of energy dependence function using the desired energy for decomposition.

In accordance with still another aspect of the disclosure, a medical imaging system is provided that includes an x-ray source configured to deliver x-rays to an imaging patient at a single, selected x-ray energy spectrum. The medical imaging system also includes a controller configured to control the x-ray source to acquire a single energy spectrum x-ray dataset from the imaging patient at the single, selected x-ray energy spectrum and a material decomposition image reconstruction system. The material decomposition image reconstruction system includes a material basis generator configured to decompose the single energy spectrum x-ray dataset into at least two material basis images, an en-chroma generator configured to regularize the material basis generator by enforcing an effective energy constraint, and a sinogram generator configured to generate projection data for the at least two material basis images.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Figure 1:
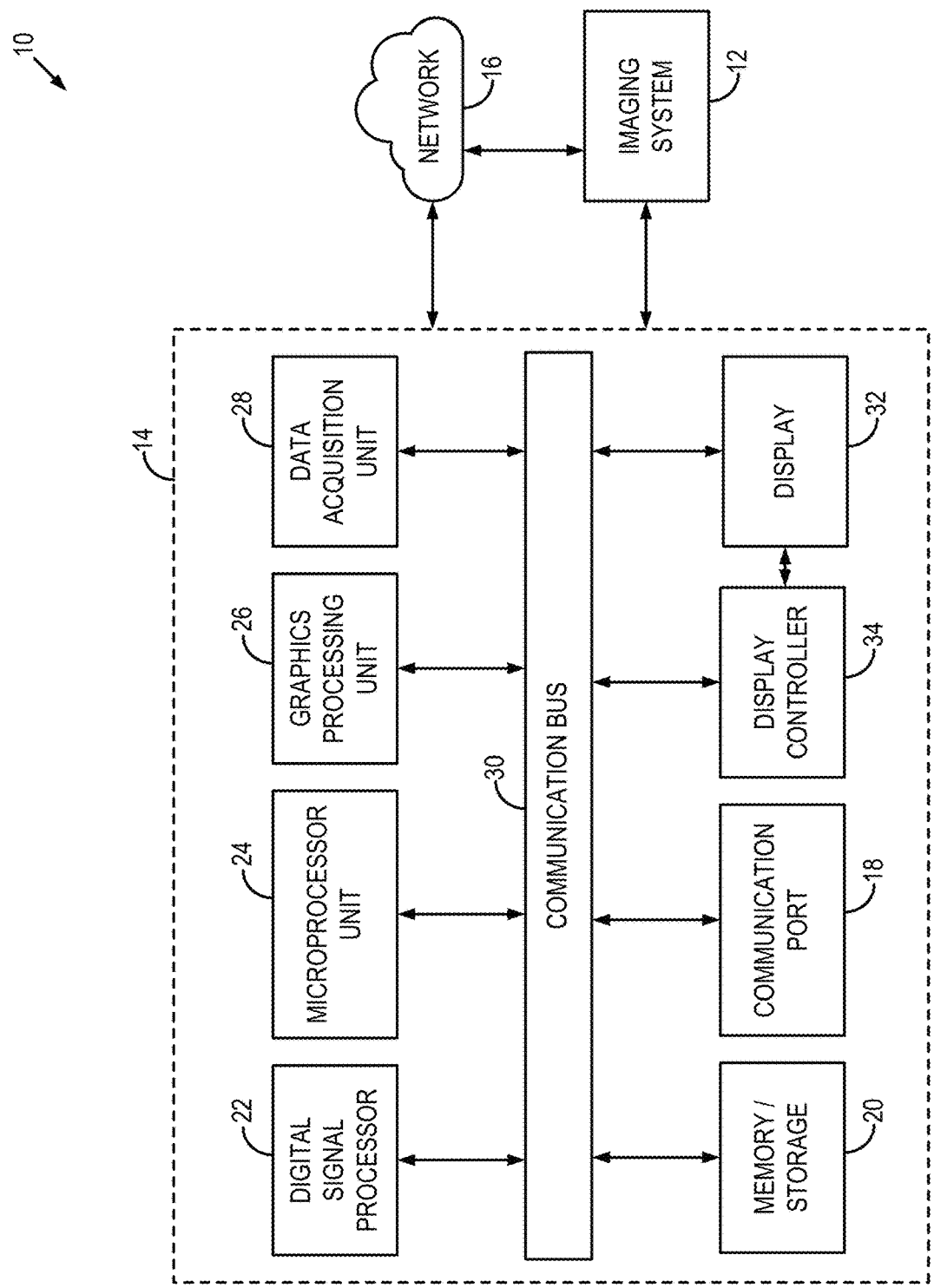
FIG. 1 is a schematic diagram of an example computer system that can be configured to implement the methods described herein.

Referring now to FIG. 1, a block diagram of an example system 10 is provided that can be configured to carry out techniques, methods, and processes accordance with the present disclosure. The system may include an imaging system 12 that is coupled to a computer system 14. The coupling of the imaging system 12 to the computer system 14 may be a direct or dedicated network connection, or may be through a broad network 16, such as an intranet or the Internet.

The computer system 14 may be a workstation integrated with or separate from the medical imaging systems 12 or a variety of other medical imaging systems, including, as non-limiting examples, computed tomography (CT) system, magnetic resonance imaging (MRI) systems, positron emission tomography (PET) systems, single photon emission computed tomography (SPECT) systems, and the like. Furthermore, the computer system 14 may be a workstation integrated within the medical imaging system 12 or may be a separate workstation or mobile device or computing system. To this end, the following description of particular hardware and configurations of the hardware of the example computer system 14 is for illustrative purposes. Some computer systems may have varied, combined, or different hardware configurations.

Medical imaging data acquired by the medical imaging system 12 or other imaging system can be provided to the computer system 14, such as over the network 16 or from a storage device. To this end, the computer system 14 may include a communications port or other input port 18 for communication with the network 16 and system coupled thereto. Also, the computer system 14 may include memory and storage capacity 20 to store and access data or images.

In some configuration, computer system 14 may include one or more processing systems or subsystems. That is, the computer system 14 may include one or more physical or virtual processors. As an example, the computer system 14 may include one or more of a digital signal processor (DSP) 22, a microprocessor unit (MPU) 24, and a graphics processing unit (GPU) 26. If the computer system 14 is integrated into the medical imaging system, a data acquisition unit 28 may be connected directly to the above-described processor(s) 22, 24, 26 over a communications bus 30, instead of communicating acquired data or images via the network 16. As an example, the communication bus 30 can be a group of wires, or a hardwire used for switching data between the peripherals or between any component, such as the communication buses described above.

The computer system 14 may also include or be connected to a display 32. To this end, the computer system 14 may include a display controller 34. The display 32 may be a monitor connected to the computer system 14 or may be integrated with the computer system 14, such as in portable computers or mobile devices.

Figure 2A:
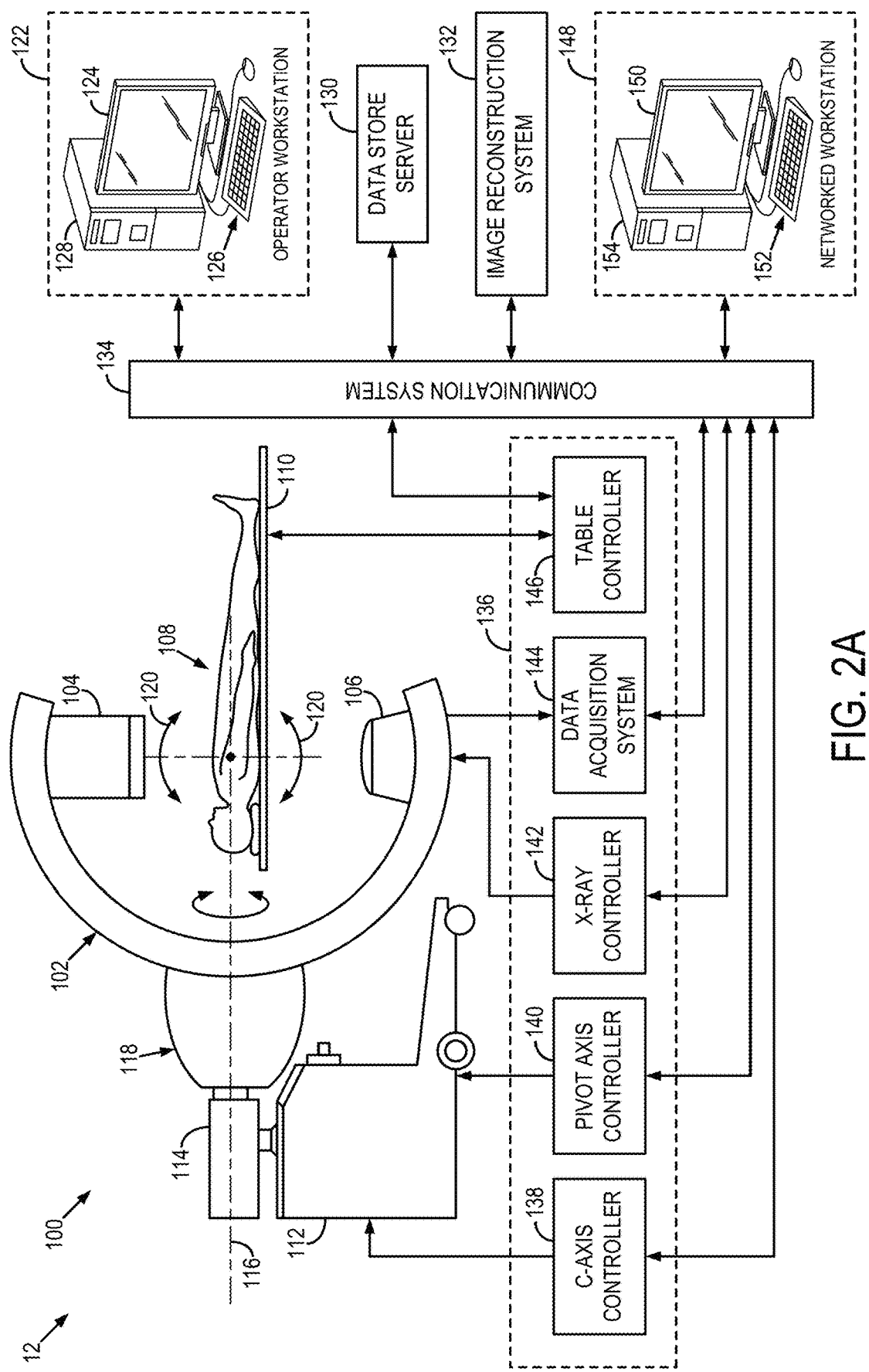
FIG. 2A is a schematic diagram of a C-arm x-ray computed tomography (CT) imaging system configured in accordance with the present disclosure.
Figure 2B:
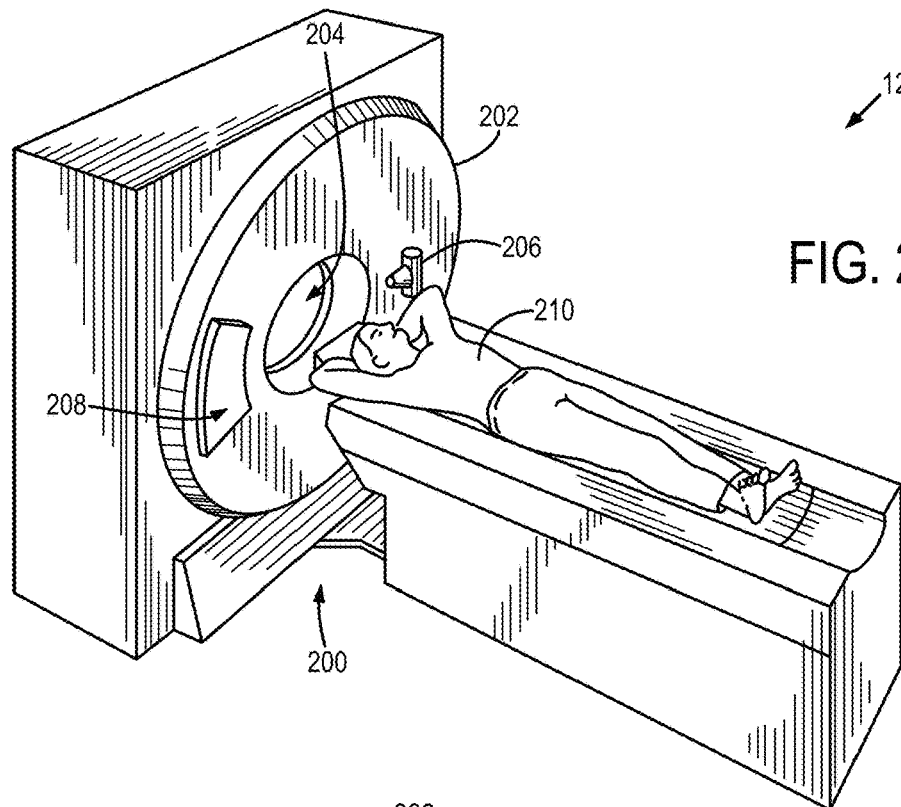
FIG. 2B is a perspective view of an example of an x-ray computed tomography (CT) system.

Referring to FIG. 2A, one, non-limiting example of the imaging system 12 of FIG. 1 is provided. Specifically, in this example, a so-called "C-arm" x-ray imaging system 100 is illustrated for use in accordance with some aspects of the present disclosure. Such an imaging system is generally designed for use in connection with interventional procedures. Such systems stand in contrast to, for example, traditional computed tomography (CT) systems 200, such as illustrated in FIG. 2B, which may also serve as an example of the imaging system 12 of FIG. 1.

Referring again to FIG. 2A, the C-arm x-ray imaging system 100 includes a gantry 102 having a C-arm to which an x-ray source assembly 104 is coupled on one end and an x-ray detector array assembly 106 is coupled at its other end. The gantry 102 enables the x-ray source assembly 104 and detector array assembly 106 to be oriented in different positions and angles around a subject 108, such as a medical patient or an object undergoing examination, which is positioned on a table 110. When the subject 108 is a medical patient, this configuration enables a physician access to the subject 108.

The x-ray source assembly 104 includes at least one x-ray source that projects an x-ray beam, which may be a fan-beam or cone-beam of x-rays, towards the x-ray detector array assembly 106 on the opposite side of the gantry 102. The x-ray detector array assembly 106 includes at least one x-ray detector, which may include a number of x-ray detector elements. Examples of x-ray detectors that may be included in the x-ray detector array assembly 106 include flat panel detectors, such as so-called "small flat panel" detectors. Such a detector panel allows the coverage of a field-of-view of approximately twelve centimeters.

Together, the x-ray detector elements in the one or more x-ray detectors housed in the x-ray detector array assembly 106 sense the projected x-rays that pass through a subject 108. Each x-ray detector element produces an electrical signal that may represent the intensity of an impinging x-ray beam and, thus, the attenuation of the x-ray beam as it passes through the subject 108. In some configurations, each x-ray detector element is capable of counting the number of x-ray photons that impinge upon the detector. During a scan to acquire x-ray projection data, the gantry 102 and the components mounted thereon rotate about an isocenter of the C-arm x-ray imaging system 100.

The gantry 102 includes a support base 112. A support arm 114 is rotatably fastened to the support base 112 for rotation about a horizontal pivot axis 116. The pivot axis 116 is aligned with the centerline of the table 110 and the support arm 114 extends radially outward from the pivot axis 116 to support a C-arm drive assembly 118 on its outer end. The C-arm gantry 102 is slidably fastened to the drive assembly 118 and is coupled to a drive motor (not shown) that slides the C-arm gantry 102 to revolve it about a C-axis, as indicated by arrows 120. The pivot axis 116 and C-axis are orthogonal and intersect each other at the isocenter of the C-arm x-ray imaging system 100, which is indicated by the black circle and is located above the table 110.

The x-ray source assembly 104 and x-ray detector array assembly 106 extend radially inward to the pivot axis 116 such that the center ray of this x-ray beam passes through the system isocenter. The center ray of the x-ray beam can thus be rotated about the system isocenter around either the pivot axis 116, the C-axis, or both during the acquisition of x-ray attenuation data from a subject 108 placed on the table 110. During a scan, the x-ray source and detector array are rotated about the system isocenter to acquire x-ray attenuation projection data from different angles. By way of example, the detector array is able to acquire thirty projections, or views, per second.

The C-arm x-ray imaging system 100 also includes an operator workstation 122, which typically includes a display 124; one or more input devices 126, such as a keyboard and mouse; and a computer processor 128. The computer processor 128 may include a commercially available programmable machine running a commercially available operating system. The operator workstation 122 provides the operator interface that enables scanning control parameters to be entered into the C-arm x-ray imaging system 100. In general, the operator workstation 122 is in communication with a data store server 130 and an image reconstruction system 132. By way of example, the operator workstation 122, data store sever 130, and image reconstruction system 132 may be connected via a communication system 134, which may include any suitable network connection, whether wired, wireless, or a combination of both. As an example, the communication system 134 may include both proprietary or dedicated networks, as well as open networks, such as the Internet.

The operator workstation 122 is also in communication with a control system 136 that controls operation of the C-arm x-ray imaging system 100. The control system 136 generally includes a C-axis controller 138, a pivot axis controller 140, an x-ray controller 142, a data acquisition system (DAS) 144, and a table controller 146. The x-ray controller 142 provides power and timing signals to the x-ray source assembly 104, and the table controller 146 is operable to move the table 110 to different positions and orientations within the C-arm x-ray imaging system 100.

The rotation of the gantry 102 to which the x-ray source assembly 104 and the x-ray detector array assembly 106 are coupled is controlled by the C-axis controller 138 and the pivot axis controller 140, which respectively control the rotation of the gantry 102 about the C-axis and the pivot axis 116. In response to motion commands from the operator workstation 122, the C-axis controller 138 and the pivot axis controller 140 provide power to motors in the C-arm x-ray imaging system 100 that produce the rotations about the C-axis and the pivot axis 116, respectively. For example, a program executed by the operator workstation 122 generates motion commands to the C-axis controller 138 and pivot axis controller 140 to move the gantry 102, and thereby the x-ray source assembly 104 and x-ray detector array assembly 106, in a prescribed scan path.

The DAS 144 samples data from the one or more x-ray detectors in the x-ray detector array assembly 106 and converts the data to digital signals for subsequent processing. For instance, digitized x-ray data is communicated from the DAS 144 to the data store server 130. The image reconstruction system 132 then retrieves the x-ray data from the data store server 130 and reconstructs an image therefrom. The image reconstruction system 130 may include a commercially available computer processor, or may be a highly parallel computer architecture, such as a system that includes multiple-core processors and massively parallel, high-density computing devices. Optionally, image reconstruction can also be performed on the processor 128 in the operator workstation 122. Reconstructed images can then be communicated back to the data store server 130 for storage or to the operator workstation 122 to be displayed to the operator or clinician.

The C-arm x-ray imaging system 100 may also include one or more networked workstations 148. By way of example, a networked workstation 148 may include a display 150; one or more input devices 152, such as a keyboard and mouse; and a processor 154. The networked workstation 148 may be located within the same facility as the operator workstation 122, or in a different facility, such as a different healthcare institution or clinic.

The networked workstation 148, whether within the same facility or in a different facility as the operator workstation 122, may gain remote access to the data store server 130, the image reconstruction system 132, or both via the communication system 134. Accordingly, multiple networked workstations 148 may have access to the data store server 130, the image reconstruction system 132, or both. In this manner, x-ray data, reconstructed images, or other data may be exchanged between the data store server 130, the image reconstruction system 132, and the networked workstations 148, such that the data or images may be remotely processed by the networked workstation 148. This data may be exchanged in any suitable format, such as in accordance with the transmission control protocol (TCP), the Internet protocol (IP), or other known or suitable protocols.

Figure 2C:
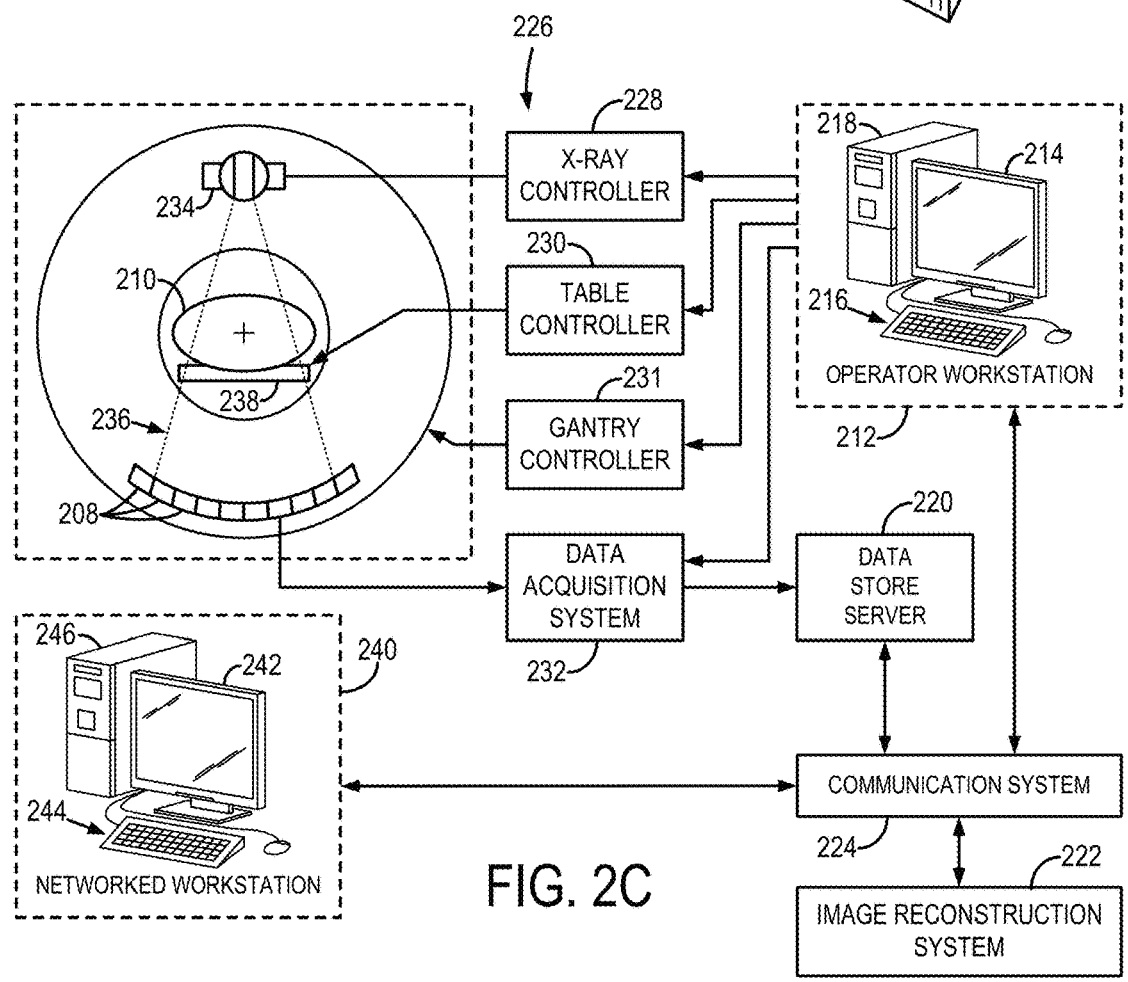
FIG. 2C is a block diagram of CT system, such as illustrated in FIG. 2B.

Similarly, referring to FIGS. 2B and 2C, the imaging system 12 may include a traditional CT system 200, which includes a gantry 202 that forms a bore 204 extending therethrough. In particular, the gantry 202 has an x-ray source 206 mounted thereon that projects a fan-beam, or cone-beam, of x-rays toward a detector array 208 mounted on the opposite side of the bore 204 through the gantry 202 to image the subject 210.

The CT system 200 also includes an operator workstation 212, which typically includes a display 214; one or more input devices 216, such as a keyboard and mouse; and a computer processor 218. The computer processor 218 may include a commercially available programmable machine running a commercially available operating system. The operator workstation 212 provides the operator interface that enables scanning control parameters to be entered into the CT system 200. In general, the operator workstation 212 is in communication with a data store server 220 and an image reconstruction system 222 through a communication system or network 224. By way of example, the operator workstation 212, data store sever 220, and image reconstruction system 222 may be connected via a communication system 224, which may include any suitable network connection, whether wired, wireless, or a combination of both. As an example, the communication system 224 may include both proprietary or dedicated networks, as well as open networks, such as the Internet.

The operator workstation 212 is also in communication with a control system 226 that controls operation of the CT system 200. The control system 226 generally includes an x-ray controller 228, a table controller 230, a gantry controller 231, and a data acquisition system (DAS) 232. The x-ray controller 228 provides power and timing signals to the x-ray module(s) 234 to effectuate delivery of the x-ray beam 236. The table controller 230 controls a table or platform 238 to position the subject 210 with respect to the CT system 200.

The DAS 232 samples data from the detector 208 and converts the data to digital signals for subsequent processing. For instance, digitized x-ray data is communicated from the DAS 232 to the data store server 220. The image reconstruction system 222 then retrieves the x-ray data from the data store server 220 and reconstructs an image therefrom. The image reconstruction system 222 may include a commercially available computer processor, or may be a highly parallel computer architecture, such as a system that includes multiple-core processors and massively parallel, high-density computing devices. Optionally, image reconstruction can also be performed on the processor 218 in the operator workstation 212. Reconstructed images can then be communicated back to the data store server 220 for storage or to the operator workstation 212 to be displayed to the operator or clinician.

The CT system 200 may also include one or more networked workstations 240. By way of example, a networked workstation 240 may include a display 242; one or more input devices 244, such as a keyboard and mouse; and a processor 246. The networked workstation 240 may be located within the same facility as the operator workstation 212, or in a different facility, such as a different healthcare institution or clinic.

The networked workstation 240, whether within the same facility or in a different facility as the operator workstation 212, may gain remote access to the data store server 220 and/or the image reconstruction system 222 via the communication system 224. Accordingly, multiple networked workstations 240 may have access to the data store server 220 and/or image reconstruction system 222. In this manner, x-ray data, reconstructed images, or other data may be exchanged between the data store server 220, the image reconstruction system 222, and the networked workstations 212, such that the data or images may be remotely processed by a networked workstation 240. This data may be exchanged in any suitable format, such as in accordance with the transmission control protocol (TCP), the Internet protocol (IP), or other known or suitable protocols.

Using the above-described systems, the structural information of an image object is encoded into the x-ray beam when the x-ray photons penetrate through the image object and are attenuated via physical interaction processes. The value of the x-ray attenuation coefficients is dependent on both the material's elemental composition and the energy of the x-ray beam. The present disclosure recognizes that, due to the use of polychromatic x-ray sources in current medical CT imaging, x-ray photons with a wide range of energies are actually used to encode structural information of the image object into the measured data. In other words, the spectral information for a given image object is already encoded in the measured sinogram data even if the measurements are performed with a single polychromatic x-ray spectrum.

Even when the polychromatic nature of so-called "single energy spectrum" or "non-dual energy spectra" system was recognized, there was no mechanism to extract this spectral information for any use. To the contrary, the polychromatic nature of x-ray sources has generally been viewed as undesirable. As such, methods have been devised to suppress the spectral effects, for example, including algorithms to reduce beam hardening artifacts, which is one of the most pronounced spectral effects in conventional single energy spectrum CT imaging.

Breaking from these understandings, the present disclosure provides systems and methods to decode spectral information in single energy spectrum or single-kV acquisitions when energy integration detectors are used and to create spectrally-resolved images, such as to differentiate objects with different elemental compositions. That is, the present disclosure breaks the historical understanding that CT-based material decomposition or spectral encoding requires at least two data sets acquired using at least two distinct energies.

In conventional single energy spectrum CT acquisitions, an x-ray source emits a polychromatic spectrum of x-ray photons. When polychromatic x-rays pass through an image object, the value of x-ray attenuation coefficients depends on material composition and the photon energy. This physical process can be modeled by the polychromatic Beer-Lambert law:

$$y_i = -\ln[\int_0^{E_{max}} d\varepsilon \Omega(\varepsilon) \exp(-\int_{l_i} dl \mu(\vec{x},\varepsilon))] \qquad (3);$$

where, $y_i$ denotes the line integral value for the i-th integral line, $E_{max}$ denotes the maximal energy determined by the tube potential, $\Omega(\varepsilon)$ denotes the joint contribution of the energy distribution of entrance photons and energy response of the detector $\mu(\vec{x}, \varepsilon)$ denotes the energy dependent linear attenuation coefficients of interest, which can be represented as a line integral of the linear attenuation coefficient of image object along the i-th integral line.

According to the mean value theorem in calculus, for any measured signal, there exists an effective energy, $\varepsilon_i$, which is somewhere between zero and the maximal energy $E_{max}$, such that:

$$y_i = -\ln[\exp(-\int_{l_i} dl \mu(\vec{x},\varepsilon_i))\int_0^{E_{max}} d\varepsilon \Omega(\varepsilon)] = \int_{l_i} dl \mu(\vec{x},\varepsilon_i) \qquad (4);$$

where, $\varepsilon_i$, denotes the beam effective energy for i-th x-ray path. Here, $\Omega(\varepsilon)$ is assumed to be normalized.

Over the diagnostic x-ray energy range (20 keV to 140 keV), photoelectric absorption and Compton scattering are the two dominant x-ray photon processes. Since interactions between material and x-ray photons are independent to the property of material, the energy dependent attenuation coefficient of interest can be decomposed as a linear combination of a limited number of products of spatially-dependent and energy-dependent components:

$$\mu(\vec{x},\varepsilon_i) = c_1(\vec{x})b_1(\varepsilon_i) + c_2(\vec{x})b_2(\varepsilon_i) \qquad (5);$$

where, $c_1(\vec{x})$ denotes the spatial distribution of photoelectric coefficients, $c_2(\vec{x})$ denotes the spatial distribution of Compton coefficients, $b_1(\varepsilon_i)$ denotes the energy-dependent photoelectric component, and $b_2(\varepsilon_i)$ denotes the energy-dependent Compton component.

Based on the linear signal model of equation 5, equation 4 can be simplified as:

$$y_i = \int_{l_i} dl \mu(\vec{x},\varepsilon_i) = \int_{l_i} dl [c_1(\vec{x})b_1(\varepsilon) + c_2(\vec{x})b_2(\varepsilon)] = p_{1,i}b_1(\varepsilon_i) + p_{2,i}b_2(\varepsilon_i) \qquad (6);$$

where, $p_{1/2,i}$ denotes the line integral value of $c_{1/2}(\vec{x})$ along i-th x-ray path.

The effective energy for each x-ray beam, $\varepsilon_i$, can be defined by solving the following minimal-norm problem:

$$\hat{\varepsilon}_i = \underset{\varepsilon_i}{\operatorname{argmin}}[p_{1,i}\,b_1(\varepsilon_i) + p_{2,i}\,b_2(\varepsilon_i) - y_i]^2. \qquad (7)$$

The above optimization problem can be solved for each individual x-ray path to determine the effective energy for each measured datum. For each ray i, all possible $\varepsilon_i \in [0, E_{max}]$ can be searched, for example, using a 0.01 keV interval. Each possible value of $\varepsilon_i, C_{1/2}(\vec{x})$ can be determined from numerical simulation or experimental studies, where the ground truth material maps are provided. With this, the line integral along i-th x-ray path can be determined numerically. Thus, $\hat{\varepsilon}_i$ can be found, such that, the modeled line integral value with a specific value of $\varepsilon_i$ provides the closest value to the measured line integral $y_i$.

PROBLEM FORMULATION

Quantitative material basis imaging in CT imaging can be formulated under the maximum-a-posterior (MAP) framework. The basis of MAP image reconstruction methods depends on the knowledge of photon statistics and prior information of ideal image representation. For an ideal photon counting detector derived in this model, the number of photons received by a given detector element i follows the Poisson statistics:

$$P(X = N_i) = \frac{\overline{N}_i^{N_i} \exp(-\overline{N}_i)}{N_i!}; \quad (8)$$

where $N_i$ denotes the number of photons received at detector element i and $\overline{N}_i$ denotes the mean photon number at the detector element i. The measurements at different detector elements can be assumed to be statistically independent and, thus, the joint probability of the measured data set is given by:

$$P(N) = P(N_1, N_2, \ldots) = \Pi_i P(N_i) \quad (9).$$

Again, using the Beer-Lambert law in x-ray attenuation in matter with a linear attenuation coefficient distribution function $\mu(\vec{x}, \varepsilon)$ at spatial location $\vec{x}$ and x-ray energy $\varepsilon$, the mean photon number at i-th measurement is given by:

$$\overline{N}_i = \overline{N}_{0,i} \Sigma_\varepsilon \Omega(\varepsilon) \exp[-\int_{l_i} d\vec{x} \mu(\vec{x} \varepsilon)] \quad (10);$$

where $\overline{N}_{0,i}$ denotes the initial photon number at the i-th measurement before the photons enter the image object, $\Omega(\varepsilon)$ is a normalized energy spectral function of photons that included the impact of both the entrance x-ray energy spectral distribution and the detector energy response function, and $E_{max}$ denotes the maximal energy determined by the tube potential.

The energy dependent linear attenuation coefficient of the image object can be decomposed as a linear combination of energy dependence function $b_k(\varepsilon)$ and the corresponding expansion coefficients $a_k(\vec{x})$, as follows:

$$\mu(\vec{x}, \varepsilon) = \Sigma_k a_k(\vec{x}) b_k(\varepsilon) \quad (11);$$

where index $k=1, 2, \ldots, K$ labels the material basis that is selected for the above decomposition. Since the energy dependence for each chosen material basis is known a priori, the linear attenuation coefficients $\mu(\vec{x}, \varepsilon)$ can be generated at any desired energy, provided that the spatial location dependent coefficients (i.e., $\{a_k(\vec{x})\}_{k=1}^K$) are known. With this context in place, the present disclosure recognizes provides a basis for spectral CT imaging using a single-energy source by determining these spatial location dependent coefficients.

To obtain the conventional voxel representation for the basis image, $a_k(\vec{x})$, the basis image can be expanded into the image voxel basis functions $e_j(\vec{x})$ as follows:

$$a_k(\vec{x}) = \Sigma_j a_{k,j} e_j(\vec{x}) \quad (12);$$

where $j \in [1, N]$ and $N = N_x N_y N_z$ is the total number of image voxels. Using this voxel representation, the line integral of a material basis can be written as:

$$\int_{l_i} d\vec{x} \, a_k(\vec{x}) = \Sigma_j a_{k,j} \int_{l_i} d\vec{x} \, e_j(\vec{x}) = \Sigma_j A_{i,j} a_{k,j} = [A a_k]_i \quad (13)$$

where the M×N matrix $A \in \mathfrak{R}^{M \times N}$ denotes the system matrix and $A_{i,j}$ the (i,j)-matrix element of A. $a_k$ is the digitized and vectorized material basis image $a_k(\vec{x})$.

In x-ray CT, so-called sinogram projection data, $y_i$, is obtained by the log-transform of the measured data $N_i$ and $N_{0i}$ as follows:

$$y_i = \ln \frac{N_{0i}}{N_i}; \quad (14)$$

the corresponding statistical mean is defined as:

$$\overline{y}_i = \ln \frac{\overline{N}_{0,i}}{\overline{N}_i}.$$

Using the developed image digitized representation, one can readily obtain:

$$\overline{y}_i := f([Aa_1]_i, [Aa_2]_i, \ldots, [Aa_k]_i, \Omega) = -\ln [\Sigma_\varepsilon \Omega(\varepsilon) \exp(-\Sigma_k b_k(\varepsilon) [Aa_k]_i)] \quad (15).$$

In other words, $$\overline{N}_i = \overline{N}_{0,i} \exp(-\overline{y}_i) \quad (16);$$

where all of the image object specific information $a_k$, image object independent information (such as basis energy dependence function $b_k(\varepsilon)$), scanner and scanning protocol specific function $\Omega(\varepsilon)$, and the system matrix information are explicitly contained in $\overline{y}_i$ as shown in equation 15. Using the above mathematical formulation, a statistical learning problem is presented that, as will be described, can be solved using systems and methods referred to herein as the Deep-En-Chroma framework or system.

STATISTICAL LEARNING PROBLEM FORMULATION

More particularly, from a set of measured data $\{N_1, N_2, \ldots\}$, the joint probability function $P(N) = P(N_1, N_2, \ldots) = \Pi_i P(N_i)$ described above is the limit of the known information. The desired image object basis image vectors $a_k$ are the statistical parameters, as set forth in equation 1. Therefore, the learning problem to be addressed by the Deep-En-Chroma system is to learn the statistical parameters $a_k$ from the observed data set $\{N_1, N_2, \ldots\}$. In practice, although the entrance x-ray spectrum from x-ray tube may be experimentally determined, it is hard to determine the energy response function at each detector element. As a result, it is hard to experimentally determine the energy dependent function $\Omega(\varepsilon)$. Therefore, for the statistical problem formulation, a more ambitious learning objective is to also learn the energy dependent function $\Omega(\varepsilon)$ from the measured data set $\{N_1, N_2, \ldots\}$.

In accordance with the present disclosure, a statistical inference method is provided to solve the above statistical learning problem. According to one non-limiting example, a Bayes method may be used. In this case, the following posterior probability can be solved according to a Bayesian statistical inference principle:

$$P(\alpha_1, \alpha_2, \ldots, \alpha_K, \Omega | N) = \frac{P(\alpha_1, \alpha_2, \ldots, \alpha_K, \Omega)}{P(N)}. \quad (17)$$

Namely, given the measured data set $\{N_i, N_2, \ldots\}$, the statistical parameters $\theta = \{a_1, a_2, \ldots, a_K, \Omega\}$ and the corresponding uncertainty in parameter estimation must be determined. To perform the above parameter estimation task, the prior $P(a_1, a_2, \ldots, a_K, \Omega)$ could be explicitly introduced and then the parameters $\theta$ to maximize the posterior probability could be searched. Namely, the statistical parameters can be estimated via solving the following optimization problem:

$$\hat{\theta} = \{\widehat{a_1}, \widehat{a_2}, \ldots, \widehat{a_K}, \hat{\Omega}\} = \text{argmax}\{\ln P(N|a_1, a_2, \ldots, a_K, \Omega) + \ln P(a_1, a_2, \ldots, a_K, \Omega)\} \quad (18).$$

Unfortunately, even for K=2, the above optimization problem is highly ill-posed as can be illustrated by considering the number of unknowns and available measurements. That is, there are KN unknowns but there are only M measurements and it is often the case KN>>M in practice. Some have tried to use empirical rules to reduce the instances where the problem cannot be solved. However, these empirical rules do not provide reliable and robust results that approach clinical needs. The major challenge encountered is the justification of prior and further constraints used in the attempts to reduce the ill-posedness of the problem.

DEEP-EN-CHROMA SYSTEM

Instead, the present disclosure overcomes these shortcomings by designing an appropriate prior for solving the statistical parameter estimation problem using a supervised learning scheme. Since the ultimate learning objective is to estimate $\theta = \{a_1, a_2, \ldots, a_K, \Omega\}$ from the measured data, the learning objective is to estimate the posterior probability distribution function $P(a_1, a_2, \ldots, a_K, \Omega|N)$.

A deep neural network, which forms part of the Deep-En-Chroma system, has been designed and trained to learn the feed forward mapping $\mathcal{F}: N \mapsto \theta$, such that, the output, $Q a_1, a_2, \ldots, a_K, \Omega|N; \mathcal{F})$, of the Deep-En-Chroma can provide a good approximation for the desired posterior distribution $P(a_1, a_2, \ldots, a_K, \Omega|N)$.

Figure 3:
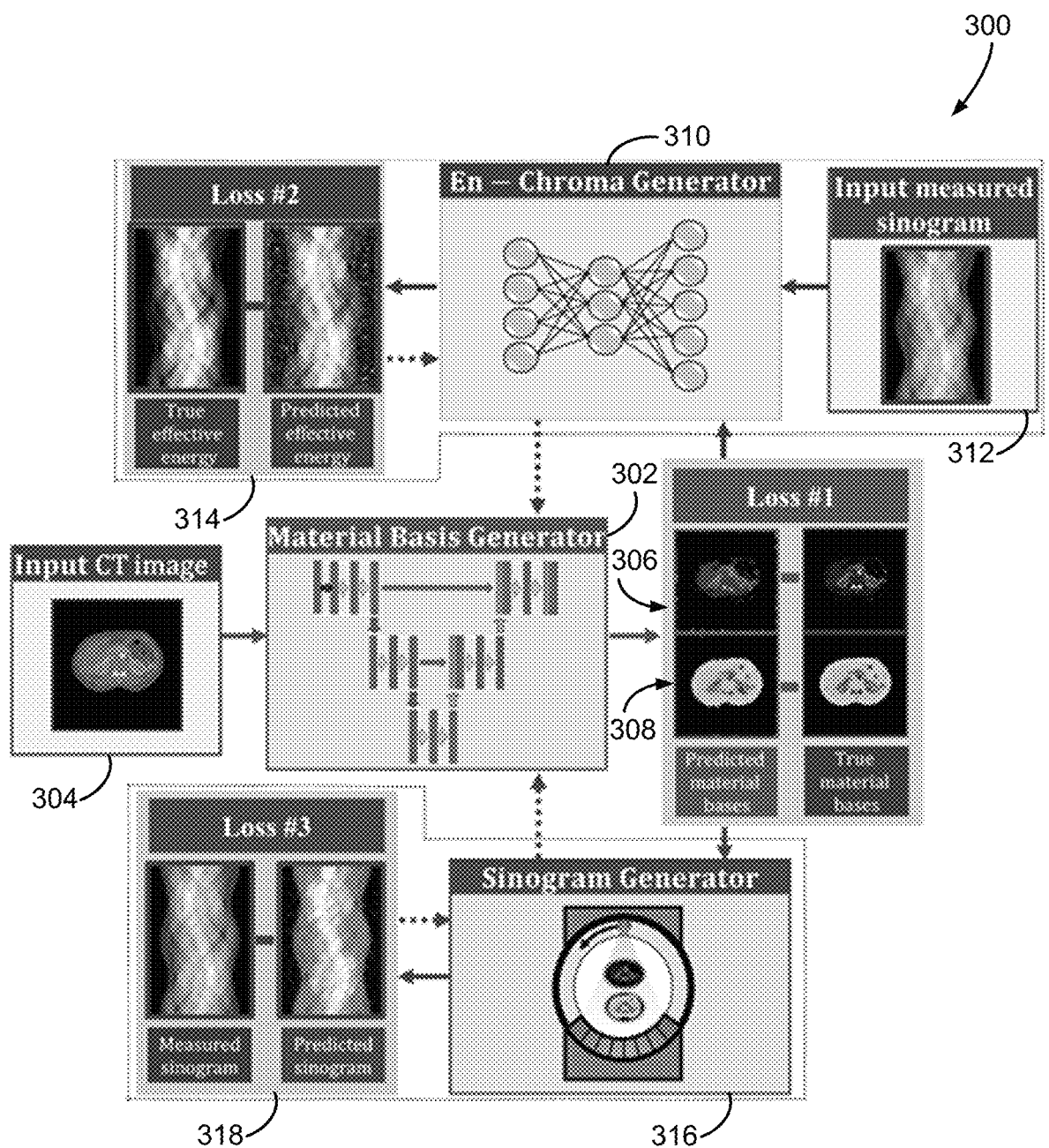
FIG. 3 is a block diagram of an image processing and/or reconstruction architecture in accordance with the present disclosure that may be utilized with or within the systems of FIGS. 1-2C and/or other imaging systems.

As will be described with respect to FIG. 3, the Deep-En-Chroma system 300 can be represented as including three specific modules with specifically defined purposes. In FIG. 3, solid arrows show the forward path and dash arrows show the backpropagation path.

The first module is the material basis generator 302. The material basis generator 302 is designed to decompose an input color-blind CT image 304 from a single-energy CT data acquisition into two material basis images 306, 308, such that the CT images at any given x-ray energy can be readily generated from the basis images and the corresponding energy dependent function as shown in equation 11. That is, the material basis generator 302 creates a color-resolving capability that has always been lost to single-energy CT systems.

The En-Chroma generator 310 is the second module. The En-Chroma generator 310 extracts the effective energy from each of the measured datum, which includes the material basis images 306, 308, an input measured sinogram 312, and effective energy information 314. Note that, due to the polychromaticity of x-ray spectrum function $\Omega(\varepsilon)$ used in data measurement, each measured data carries its own spectral information and this specific feature is characterized by the effective energy which will be further described. It is the difference in effective energy of the measured data that can be exploited to help differentiate two objects with same CT number.

The third module is the sinogram generator 316. The sinogram generator 316 processes the sinogram data and ensures that the obtained material basis images 306, 308 can indeed be used to generate the measured projection data using equation 15.

In terms of the language used in game theory in economics, the three modules represent three players that form a grand coalition in the game. The players have their specific request in gain sharing as dictated by the corresponding loss function. The model training process can thus be viewed as the negotiation process among the players to seek for an agreement such that their contributions and gains in the game are settled with maximal degree of satisfaction.

After the training of Deep-En-Chroma network is complete, it is the material basis generator that is used to generate two material basis images from a single color-blind CT images since the characteristic spectral information buried into the measured data has been extracted and encoded into the generative material basis generator module.

Figure 4:
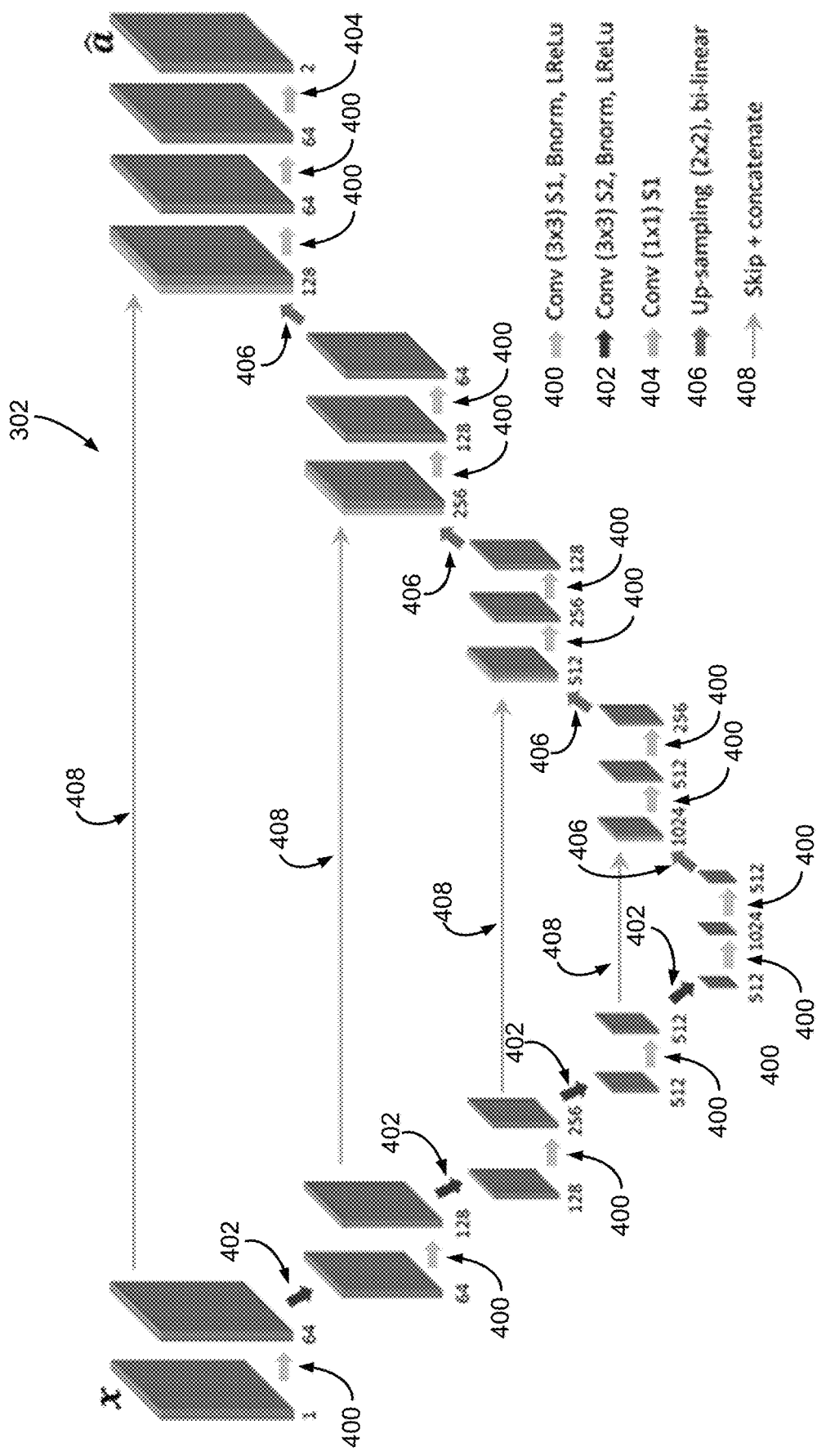
FIG. 4 is a schematic diagram of one non-limiting example of a material basis generator system in accordance with the present disclosure.

More particularly, referring to FIG. 4, the material basis generator 302 $\mathcal{B}$ takes a color-blind CT image with the dimension of N×N as its input to generate K material basis images with the dimension of N×N via a 23-layer deep neural network. In this non-limiting example, there may be three types of convolutional layers used in the material basis generator 302. The first type 400, uses 3×3 convolutional kernels with stride 1 and dented as (Cony, 3×3, S1) followed by a batch normalization operation (Bnorm) and the leaky rectified linear unit (LReLu) as its activation function. The second type 402, uses 3×3 convolutional kernels with stride 2, i.e., (Cony, 3×3, S2), followed by Bnorm and LReLu. Leaky parameter used in LReLu was set to be 0.2. The third type 404, uses 1×1 convolutional kernels with stride 1, i.e., (Cony, 1×1, S1), followed by linear function as activation.

All layers were designed with their corresponding bias terms as well. Convolutional operations in all convolutional layers were performed with padding to maintain the dimensionality to be the same. Up-sampling layers 406 were designed with 2×2 kernel size (Up-sample 2×2) and bi-linear interpolation kernels were used in all up-sampling layers. Skip and concatenation connections 408 were used to facilitate the training process through backpropagation. Kernels in convolutional layers were initialized as Glorot uniform distributed random numbers and the bias terms were initialized as zeros. In batch normalization layers, the momentum parameter was set to be 0.99 and the epsilon parameter was set to be 0.001. Beta terms were initialized as zeros and gamma terms were initialized as normal distributed random numbers with zero mean value and 0.01 standard deviation. Moving mean terms were initialized as zeros and moving variance terms were initialized as ones. Mean centering and variance scaling were used for all batch normalization layers. In this non-limiting example of a detailed design of the material basis generator 302, The number below each output tensor denotes the number of channels of the output tensor.

Figure 5:
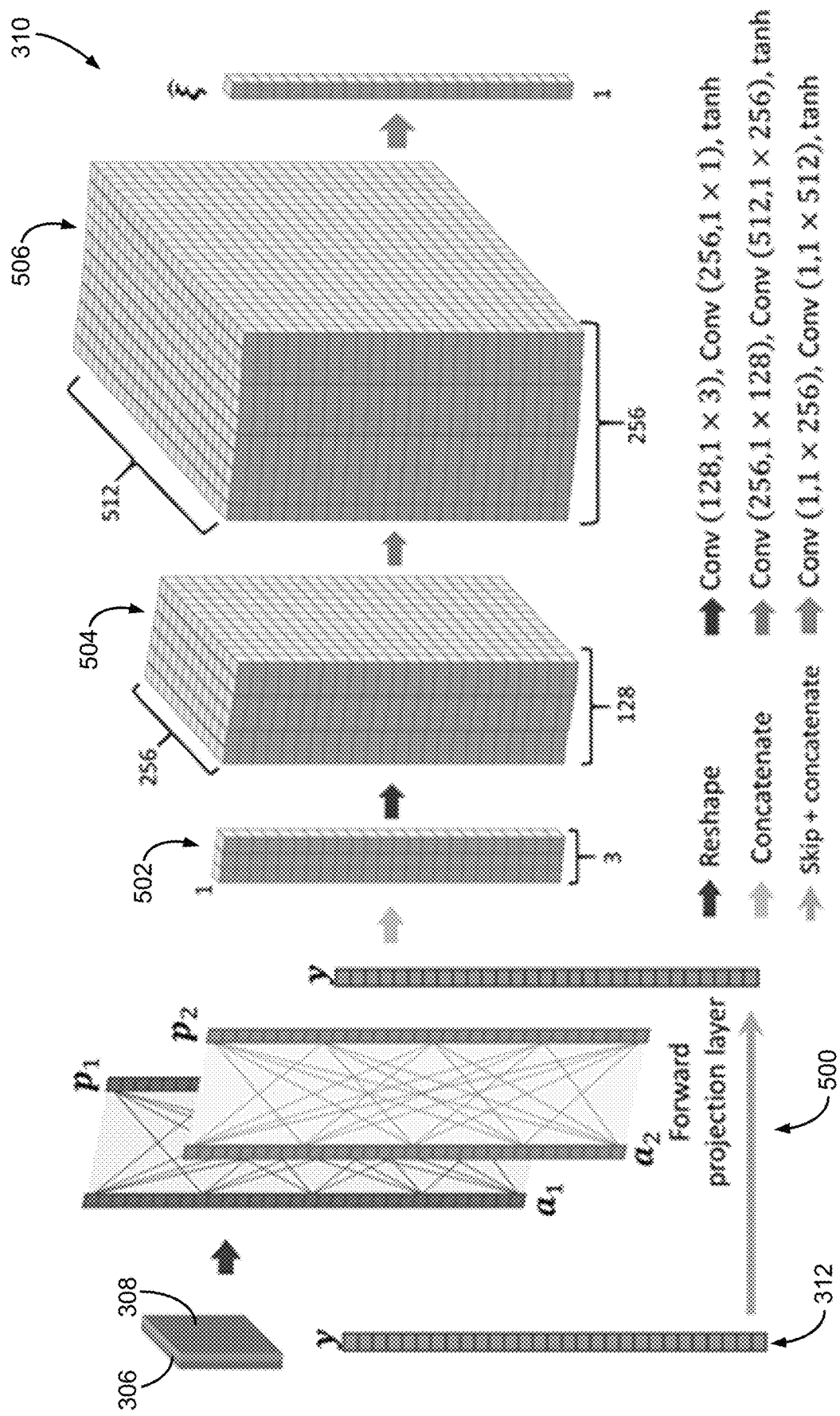
FIG. 5 is a schematic diagram of one non-limiting example of an En-Chroma generator system in accordance with the present disclosure.

Referring now to FIGS. 3 and 5, one non-limiting example of an implementation for the En-Chroma generator 310 ($\mathcal{C}$) takes the estimated line integrals of the two material basis images from the material basis generator 306, 308 and the measured sinogram 312 as its inputs to generate the effective energy distribution via a 4-layer deep neural network including a frozen forward projection layer 500 followed by three trainable convolutional layers 502, 504, 506. In the illustrated configuration, the En-Chroma generator 310 predicts the effective energy for each measured datum individually. The first convolutional layer 502 encodes the input with dimension of 3×1 to a feature space with the dimension of 128×256 along two channel directions. The second convolutional layer 504 transforms the hidden layer activations to another feature space with the dimension of 256×512. The third convolutional layer 506 transforms the hidden layer outputs to the feature space of effective energy with dimension of 1×1. After each convolutional layer, hyperbolic tangent function (tan h) was used as its activation function. Weights in convolutional layers were initialized as Glorot uniform distributed random numbers and bias terms were initialized as zeros. During the training process, the predicted effective energy from estimated material basis maps (the output of module 1) was compared against to the ground true effective energy generated from true spectral CT data acquisitions. The difference between the predicted effective energy and ground true effective energy was backpropagated to regularize parameter updates in the material basis generator.

In conventional single-kV CT acquisitions, an x-ray source emits a polychromatic spectrum of x-ray photons. When polychromatic x-rays pass through an image object, the value of x-ray attenuation coefficients depends on material composition and the photon energy. This physical process can be modeled by the polychromatic Beer-Lambert law described above in equation 11.

According to the mean value theorem for definite integrals, $\forall i$, there exists an energy $\varepsilon_i \in [0, E_{max}]$, such that:

$$y_i = -\ln[\exp(-\int_{l_i} dl \mu(\vec{x}, \varepsilon_i)) \int_0^{E_{max}} d\varepsilon \Omega(\varepsilon)] = \int_{l_i} dl \mu(\vec{x}, \varepsilon_i), \quad (19)$$

where, $\varepsilon_i$ denotes the beam effective energy for i-th x-ray path nd $E_{max}$ denotes the maximal energy determined by the tube potential.

As described above, the energy dependent attenuation coefficient of the image object can be decomposed as linear attenuation of limited number of products of spatial-dependent and energy-dependent components: $\mu(\vec{x}, \varepsilon) = \Sigma_k a_k(\vec{x}) b_k(\varepsilon)$. Based on this linear signal model, the above formulae can be simplified as:

$$y_i = \int_{l_i} dl \mu(\vec{x}, \varepsilon_i) = \Sigma_k b_k(\varepsilon_i) \int_{l_i} dl\, a_k(\vec{x}) := \Sigma_k p_{k,i} b_k(\varepsilon_i) \quad (20)$$

where, $p_{k,i}$ denotes the line integral value of $a_k(\vec{x})$ along i-th x-ray path. Therefore, the effective energy for measured projection data can be estimated by solving the following minimal-norm problem:

$$\hat{\varepsilon}_i = \operatorname{argmin}_{\varepsilon_i}[\Sigma_k p_{k,i} b_k(\varepsilon_i) - y_i]^2 \quad (21).$$

The above optimization problem can be solved for each individual x-ray path to determine the effective energy for each measured datum. For each ray i, we search for all possible $\varepsilon_i \in [0, E_{max}]$ on a 0.01 keV interval. For each possible value of $\varepsilon_i$, $\{a_k(\vec{x})\}$ are known from numerical simulation or experimental studies where the ground truth material maps are provided from dual-energy data acquisition. Once this is accomplished, the line integral along i-th x-ray path can be determined numerically. Thus, $\hat{\varepsilon}_i$ can be found, such that, the modeled line integral value with a specific value of $\varepsilon_i$ provides the closest value to the measured line integral $y_i$. For example, the effective energy calculation method can be used to generate ground true effective energy distributions for training the En-Chroma generator 310.

Figure 6:
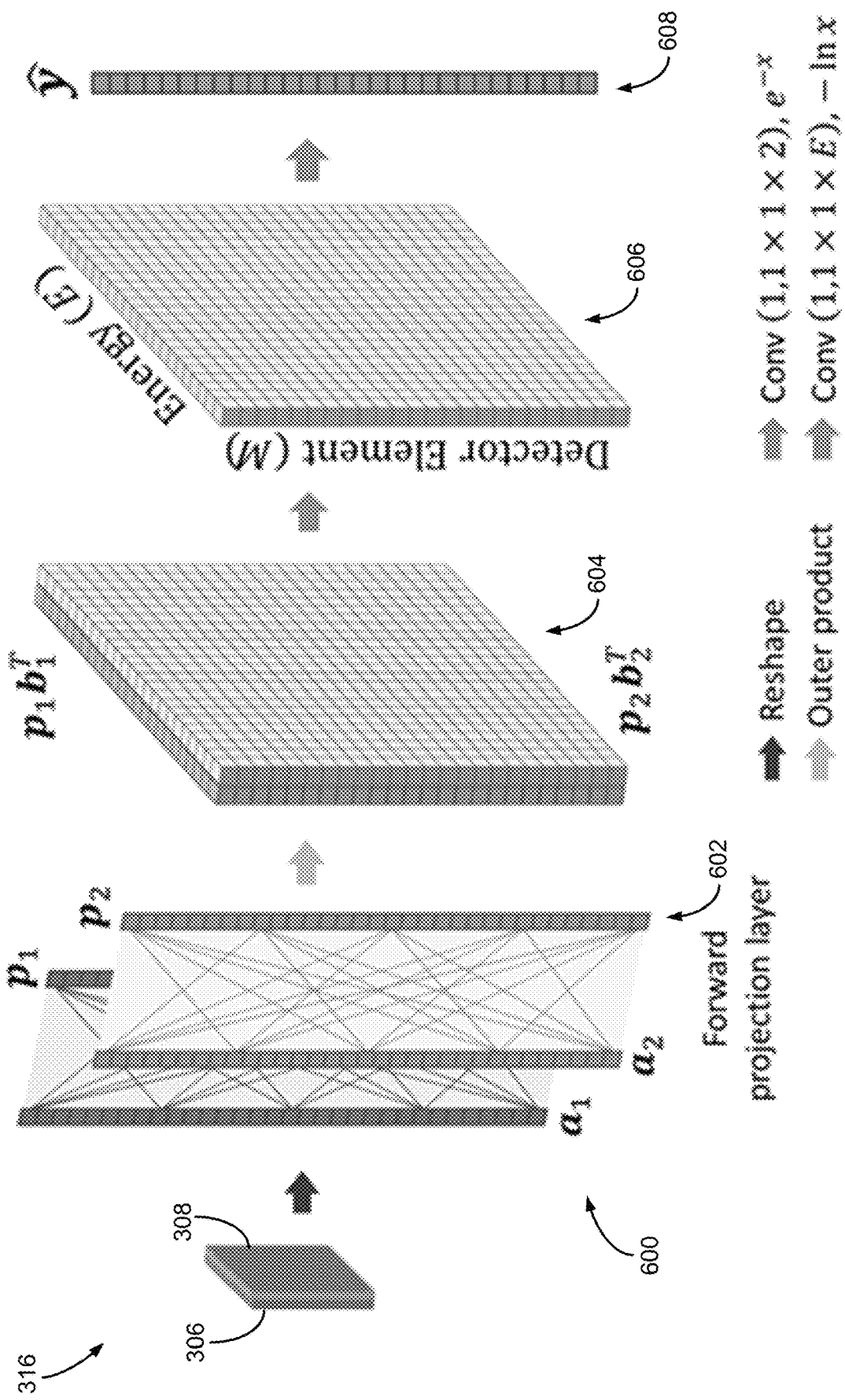
FIG. 6 is a schematic diagram of one non-limiting example of a sinogram generator system in accordance with the present disclosure.

Referring to FIGS. 3 and 6, the sinogram generator 316 ($\mathcal{S}$) takes the estimated K material basis images 306, 308 with dimension of N×N as its input to generate the estimated polychromatic sinogram with the dimension of $N_c \times N_v$ via a 4-layer deep neural network 600. The first layer 602 in the sinogram generator 316 performs the forward projection for each output channel of the material basis generator 302 individually. The second 604 and the third layer 606 generate a series of spectral-resolved monochromatic line integrals from the output of the first layer 602. The final convolutional layer 608, with 1×1 kernel size and linear activation, learns a linear combination to generate the estimated polychromatic sinogram. In the final convolutional layer, the learned weights approximate the energy response of the experimental data acquisition including x-ray tube spectrum and detector energy responses. The sinogram generator aims to ensures the predicted polychromatic sinogram approximates measured projection data.

DEEP-EN-CHROMA SYSTEM OPERATION

With this basic framework for the modules of the Deep-En-Chroma system 300, the interaction of the modules and function of the overall system can be described. The desired mapping ($\mathcal{F}$) to generate material basis maps ($\{a_k\}_{k=1}^{k}$) from input CT image and measured sinogram is approximated by a deep neural network representation by a multi-layer composition of a series of nonlinear mappings, i.e., $a = \mathcal{F}(z) \approx \hat{\mathcal{F}}(z) = h^{(L)} \circ h^{(L-1)} \circ \ldots \circ h^{(l)} \circ \ldots h^{(1)}(z)$. Here $l \in \{1, 2, \ldots, L\}$ denotes the layer index and L denotes the total number of layers and "$\circ$" denotes the function composition. To simplify the notation, a compact notation without subscript indices is introduced to denote the input-output relationship at the l-th layer as $z^{(l)} = h^{(l-1)}(z^{(l-1)})$.

Using the mean least square error as the goodness metric, a loss function can be designed to optimize for the unknown parameters ($\mathcal{B}, \mathcal{C}, \mathcal{S}$) by solving the following optimization problem:

$$\{\mathcal{B}^*, \mathcal{C}^*, \mathcal{S}^*\} = \operatorname{argmin}_{\mathcal{B}, \mathcal{C}, \mathcal{S}} \frac{1}{2N_s} \sum_i \{\lambda_1 \|\mathcal{B}(x_i) - \alpha_i\|_F^2 + \lambda_2 \|\mathcal{C}(y_i, \mathcal{B}(x_i)) - \mathcal{C}(y_i, \alpha_i)\|_2^2 + \lambda_3 \|\mathcal{S} \circ \mathcal{B}(x_i) - y_i\|_2^2\} \quad (22)$$

where, $i \in \{1, 2, \ldots, N_s\}$ denotes the index of training samples, $N_s$ denotes the total number of training samples, $\|\cdot\|_2$ denotes the L2-norm of a given vector, $\|\cdot\|_F$ denotes the Frobenius norm of a given matrix, $a = [a_1, a_2, \ldots, a_K]$ denotes the compact notation that concatenates each basis channel of the ground true material basis map, x denotes the input CT image, and y denotes the input measured sinogram data. Three hyperparameters $\lambda_1$, $\lambda_2$, and $\lambda_3$ control the relative weights of the effective energy fidelity term (the second term in the above loss function) and the data fidelity term (the third term in the above loss function). By empirically selecting the value of $\lambda_2$ and $\lambda_3$, encoded information in image domain, measured data domain and hidden spectral information (represented by effective energy of each measured datum) are jointly utilized to exact the needed spectral information from a conventional single-kV CT acquisition.

To perform the backpropagation procedure for optimizing the model parameters, the gradients in each layer can be defined. Most of the gradient computation is similar to other well-known convolutional neural networks. However, some new operations are needed for the forward projection operation used in the material basis generator 302 and the En-Chroma generator 310 (the L24 layer).

Let $\mathcal{L}$ denote the loss function and $\Theta^{(l)}$ denote the unknowns to be learned at the l-th layer. The associated gradient $$\frac{\partial \mathcal{L}}{\partial \Theta^{(l)}}$$

can be obtained through the backpropagation as:

$$\frac{\partial \mathcal{L}}{\partial \Theta^{(l)}} = \frac{\partial z^{(l+1)}}{\partial \Theta^{(l)}} \frac{\partial z^{(l+2)}}{\partial z^{(l+1)}} \cdots \frac{\partial z^{(L)}}{\partial z^{(L-1)}} \frac{\partial \mathcal{L}}{\partial z^{(L)}}. \quad (23)$$

Here three types of gradients are needed:

$$\frac{\partial z^{(l+1)}}{\partial \Theta^{(l)}} = \frac{\partial h^{(l)}(z^{(l)})}{\partial \Theta^{(l)}} \quad (24)$$

$$\frac{\partial z^{(l+2)}}{\partial z^{(l+1)}} = \frac{\partial h^{(l+1)}(z^{(l+1)})}{\partial z^{(l+1)}},$$

$$\frac{\partial \mathcal{L}}{\partial z^{(23)}} = A^T \frac{\partial \mathcal{L}}{\partial z^{(24)}}.$$

The first two gradients can be calculated using the standard numerical routines, such as those provided by Tensorflow. In equation 24, compared to the matrix A, which performs the forward projection at the output of L23 in the feedforward path, its gradient, $A^T$ performs the direct backward projection of the derivative of loss function with respect to the output of L24 in the backpropagation path to form the gradient at the L24. Here A denotes the forward projection operation and $A^T$ denotes the backward projection operation. Both A and $A^T$ can be implemented in compute unified device architecture (CUDA) and then incorporated as custom operations into numerical routines for calculating the first two gradients, such as using Tensorflow.

The En-Chroma generator 310 has an impact on the material basis generator 302. Due to the use of polychromatic x-ray sources in current medical CT imaging, the spectral information of the image object has already been encoded in the measured data even if the measurements are performed with a single polychromatic x-ray spectrum. In the past, it was not known how to extract this spectral information to be used for good, and in fact, many methods have been designed to discard the encoded spectral information. Due to the variation of effective energy carried by each measured datum, the acquired data set demonstrates spectral inconsistency and this spectral inconsistency is the root cause of beam hardening image artifacts in the reconstructed CT images. Therefore, the efforts to reduce beam hardening in the past is essentially to discard the encoded spectral information in measured data.

To illustrate how the trained En-Chroma generator 310 actually improves the material decomposition accuracy, one can observe follow the data path of FIG. 3 forward from the material basis generator 302. If the performance of the material basis generator 302 is suboptimal, it will predict a pair of inaccurate basis images 306, 308. With a pair of inaccurate material basis pairs 306, 308 (Loss #1) sent to the En-Chroma generator 310, the predicted effective energy map would also be inaccurate (Loss #2), compared to the ground true effective energy map generated from dual-energy data acquisition. This difference is reflected in its contribution to the final training loss. During the backpropagation process, the L2 norm difference between predicted and ground true effective energy maps is propagated through the backpropagation path of the En-Chroma generator 310 to fine-tune the learnable parameters in material basis generator 302. This backpropagation process is accomplished by using the gradient at the frozen forward projection layer (L24) that has been defined, for example, manually. In summary, the functionality of the En-Chroma generator 310 is to regularize the process of material basis generation by the material basis generator 302 by enforcing the effective energy constraint.

The sinogram generator 316 also has an impact on the material basis generator 302. The functionality of the sinogram generator 316 can be understood from two different aspects. On the one hand, when the performance of the material basis generator 302 is suboptimal, then the material basis generator 302 predicts a pair of inaccurate basis maps 306, 308 (Loss #1). The pair of inaccurate material basis pairs 306, 308 will then be sent to the sinogram generator 316 to produce inaccurate sinogram data when it is compared to the measured sinogram (Loss #2). In the error backpropagation process, the L2 norm difference between predicted and measured sinogram is propagated through the backpropagation path of the sinogram generator 316 to tune the learnable parameters in material basis generator 302.

On the other hand, when the performance of the material basis generator 302 is nearly optimal (Loss #1 is minimal) and, thus, the predicted material basis maps 306, 308 are nearly accurate, the difference between predicted and measured sinogram (Loss #3) may still be significant because the sinogram generator 316 may have learned an inaccurate energy response function. As previously explained, learnable parameters in the last layer in the sinogram generator (i.e. the L30) approximate the joint impact of entrance x-ray spectrum and detector energy response function. If the learned joint energy response deviates from that used in numerical simulation or experimental data acquisition, the difference between predicted and measured sinogram (Loss #3) may still be significant. During the backpropagation process, the L2 norm difference between predicted and measured sinogram is propagated through the backpropagation path of the sinogram generator 316 to fine-tune the learnable parameters in L30. In the end, the learned joint energy response approximates that used experiment data acquisitions.

TRAINING

To configure the Deep-En-Chroma system 300 to operate at best performance, a variety of non-limiting training strategies were developed for the system. The acquired training data set included basis images, effective energy for each measured projection datum, and the sinogram projection data. These prepared training data were used to train the entire Deep-En-Chroma system 300 in two stages:

Stage 1: Pretraining of three individual modules

To pretrain the material basis generator 302, the training loss was obtained by setting $\lambda\_1=1, \lambda\_2=\lambda\_3=0$ in equation 9. Similarly, to pretrain the En-Chroma generator 310, the training loss was obtained by setting $\lambda\_2=1, \lambda\_1=\lambda\_3=0$ in equation 9.

Stage 2: End-to-end training all three modules together

Following the pre-training of each individual module, an end-to-end global training is performed using the above two inputs (Sinogram and DICOM CT image) and all three outputs (basis image output, effective energy output, and sinogram output) in a weighted combination of the three training loss functions. In the global end-to-end training phase, an empirical two-step alternating training strategy was been employed. Within each training epoch, the entire training dataset was randomly distributed to 500 mini-batches. For each given mini-batch, one of the two hyper-parameters in the loss function ($\lambda\_2$ or $\lambda\_3$) was set to 0. To be more specific, at the current mini-batch, the model was trained only with material bases loss and effective energy loss, namely, $\lambda\_1=1, \lambda\_2=0.1, \lambda\_3=0$ were used in this mini-batch. For the next adjacent mini-batch, the model was trained only with material bases loss and data fidelity loss, namely, $\lambda\_1=1, \lambda\_2=0, \lambda\_3=0.05$ were used. After all mini-batches were used to minimize the loss function, the same two-step alternating strategy is used for the next epoch.

The stochastic gradient descent with momentum was used as the optimizer in this training. Learning rate ($\eta = [10]^{\wedge}(-3)$) and momentum ($\beta=0.9$) were empirically selected. Although there was no theoretical guarantee of convergence for the empirical two-step alternating training strategy, empirical convergence was confirmed by monitoring the change of loss function value with respect to each epoch and showed that the two-step alternating strategy decreases the loss function value quasi-monotonically, and indicates the empirical convergence of the numerical process.

Pretraining of the Deep-En-Chroma system 300, especially for pretraining of the En-Chroma generator 310 utilized high quality training samples for effective energy distribution. Clinical CT images-based numerical simulations were conducted to provide high quality training samples and the needed anatomical complexity for the pretraining phase. In the numerical simulation data acquisition, clinical CT image volumes, each containing 150-250 image slices, were used to generate simulation training data by using a standard ray-driven numerical forward projection procedure in a fan-beam geometry. The geometrical parameters for the numerical simulation are the same as that used in a clinical 64-slice multi-detector row CT scanner. To make the simulated dataset as realistic as possible (i.e. with realistic anatomical structures) and to facilitate for further generalization to human subjects with complex anatomy, a density-scaling-based simulation method is used in numerical simulations. The method contained the following steps.

From clinical contrast-enhanced CT images, a total of 10,000 pairs of representative calcium and iodine concentration levels ($C_{ca}$ and $C_I$) were predetermined. Iodine-containing organs such as the coronary arteries and cardiac chambers are assumed to be composed of both water and the pre-selected iodine solution with concentration $C_I$. Bony structures are assumed to be composed of both water and the pre-selected calcium solution with concentration $C_{ca}$. The mass attenuation coefficient of an iodine-containing pixel can be represented as follows:

$$\left(\frac{\mu}{\rho}\right)_{w+I}(\varepsilon) = f_w \left(\frac{\mu}{\rho}\right)_w(\varepsilon) + f_I \left(\frac{\mu}{\rho}\right)_I(\varepsilon); \quad (25)$$

where f denotes the weight fraction. The mass attenuation of each calcium-containing pixel can be modeled using the similar method. For clarity, a step-by-step procedure to generate the numerical simulation data is presented as follows:

1) An image-based segmentation technique can be used to segment each clinical CT image into a water mask (denoted as $M_w$), an iodine solution mask (denoted as $M_{iodI}$), a calcium solution mask (denoted as $M_{ca}$), and an air mask (denoted as $M_{air}$).

2) For a given CT system and x-ray spectrum, the effective beam energy $\bar{\varepsilon}$ was estimated via a calibration process.

3) The CT image with units of HU was converted to $\mu(\vec{x}, \vec{\varepsilon})$ using $$\mu(\vec{x}, \bar{\varepsilon}) = \left(\frac{HU}{1000} + 1\right)\mu_w(\bar{\varepsilon}).$$

4) For a CT image pixel falling into the $i^{th}$ material mask, the density of the tissue in that pixel was estimated using $$\rho(\vec{x}) = \frac{\mu(\vec{x}, \bar{\varepsilon})}{\left(\frac{\mu}{\rho}\right)_i(\bar{\varepsilon})},$$

where $$\left(\frac{\mu}{\rho}\right)_i(\bar{\varepsilon})$$

is the mass attenuation coefficient of the $i^{th}$ material at energy level $\bar{\varepsilon}$.

5) The linear attenuation coefficient of the pixel at an arbitrary energy level $\varepsilon$ was estimated using $$\mu(\vec{x}, \varepsilon) = \rho(\vec{x})\left(\frac{\mu}{\rho}\right)_i(\varepsilon).$$

The process in 1)-5) was repeated for all pixels in the image.

6) Monoenergetic sinograms at different $\varepsilon$ (40 to 140 keV) were generated via numerical forward projection.

7) A polychromatic sinogram was synthesized from the monoenergetic sinograms and the polychromatic x-ray spectrum.

To collect data for the training of Deep-En-Chroma system 300, anthropomorphic phantoms were scanned that included (i) a head phantom (PH-3 ACS Head, Kyoto Kagaku, Japan), (ii) a multipurpose anthropomorphic phantom (Lungman, Kyoto Kagaku, Japan); (iii) an abdominal CT phantom with a custom tumor insert that contains multiple simulated liver lesions (CIRS Triple Modality 3D Abdominal Phantom, Norfolk, Va.); and (iv) the Gammex spectral CT phantom (Gammex, Middleton, Wis.) that provides users with the ability to perform quality assurance for spectral CT analysis of iodine and calcium. Training data acquisitions were performed using the GE 64-slice Discovery CT 750 HD. All phantoms were scanned at 80 kV, 100 kV, 120 kV, and 140 kV to acquire the training data. From the acquired data, the following training labels was generated: (i) material-basis maps for (water, bone) and (water, iodine) and (ii) sinogram data for each given scan have been obtained using a proprietary software toolkit provided by GE Healthcare. The CT images from the 80 and 140 kV scans were paired to perform image-domain material decomposition to generate the needed material basis training labels. A total of 5,000 CT scans were performed to acquire more than 1.0 million data pairs to train the network and test its performance. For each phantom, 90% of the acquired data has been used for training purposes and 10% of the data was allocated as test data to ensure that there is no overfitting in the training process of Deep-En-Chroma system 300.

The training data sets were acquired using the GE 64-slice Discovery CT750 HD scanner. This CT system is equipped with the GE fast kV switching technique known as Gemstone Spectral Imaging (GSI) (GE Healthcare, Wis.). All phantoms were scanned at 80 kV, 100 kV, 120 kV, and 140 kV at a variety of exposure levels ranging from 10 mAs to 500 mAs to acquire training data. From the acquired data, the following training labels have been generated: (1) material basis images (water, calcium) and (water, iodine). The images from the 80 kV scan and the 140 kV scan were paired to perform image-domain material decomposition to generate basis images for each scanned phantom in order to obtain the training label basis images. (2) Label images for the effective energy feature "En-Chroma Generator" module. From the ground truth basis images, a forward projection operation is performed to generate the corresponding line integrals for each given ray. This step yields two line integrals, $p_{1,i}$ and $p_{2,i}$ for the two corresponding material basis images respectively. The nonlinear optimization problem (equation 11) was then solved to obtain the effective energy, $\varepsilon_i$, and used as the training label for the "En-Chroma" module in the Deep-En-Chroma system. (3) Sinogram data, i.e. $y_i$ values, for each given scan were obtained. The same procedures were performed to generate training datasets for numerical simulated datasets.

Thus, it was shown that an implementation of a Deep-En-Chroma system could be designed and trained to achieve spectral CT imaging using an energy integration detector and a single-energy acquisition. Both physical phantom studies and human subject studies demonstrate the clinical feasibility of generating quantitative iodine maps to detect lung perfusion defect for pulmonary embolism diagnosis.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for performing material decomposition using a single energy spectrum x-ray dataset, the system comprising:
   a material basis generator configured to decompose the single energy spectrum x-ray dataset into at least two material basis images;
   an en-chroma generator configured to regularize the material basis generator by enforcing an effective energy constraint; and
   a sinogram generator configured to generate projection data from the at least two material basis images.

2. The system of claim 1 wherein the en-chroma generator is configured to extract the effective energy from each datum in the single energy spectrum x-ray dataset, including the at least two material basis images.

3. The system of claim 1 wherein the material basis generator is configured to extract energy dependent linear attenuation coefficients for each image object in the single energy spectrum dataset to decompose the single energy spectrum dataset as a linear combination of energy dependence function $b_k(\varepsilon)$, and corresponding expansion coefficients $a_k(\vec{x})$, wherein $\vec{x}$ is a selected spatial location, $\varepsilon$ is an x-ray energy in the single energy spectrum x-ray dataset at the selected spatial location, and k=1, 2, ..., K, to serve as an index that labels material basis that is selected for decomposition.

4. The system of claim 3 wherein the material basis generator is configured to decompose the single energy spectrum x-ray dataset into linear attenuation coefficients, $\mu(\vec{x}, \varepsilon)$, as follows:

$$\mu(\vec{x},\varepsilon)=\Sigma_k a_k(\vec{x})b_k(\varepsilon).$$

5. The system of claim 1 wherein at least one of the material basis generator or the en-chroma generator are formed of a learning network.

6. The system of claim 1 wherein the single energy spectrum x-ray dataset is a single energy spectrum computed tomography (CT) dataset.

7. The system of claim 1 wherein the material basis generator is configured to extract energy dependent linear attenuation coefficients for each image object in the single energy spectrum x-ray dataset to decompose the single energy spectrum x-ray dataset as a linear combination of energy dependence function $b_k(\varepsilon)$, and corresponding expansion coefficients $a_k(\vec{x})$, wherein $\vec{x}$ is a selected spatial location, E is an x-ray energy in the single energy spectrum x-ray dataset at the selected spatial location, and k=1, 2, ..., K, to serve as an index that labels material basis that is selected for decomposition.

8. The system of claim 7 wherein the material basis generator is configured to generate material basis images $a_k(\vec{x})$ from the single energy spectrum x-ray dataset.

9. The system of claim 8 wherein the output of material basis generator is configured to generate energy-resolved spectral CT images, as follows: $\mu(\vec{x},\varepsilon)=\Sigma_k a_k(\vec{x})b_k(\varepsilon)$.

10. A method for performing a material decomposition using a single energy spectrum x-ray dataset, the method comprising:
    accessing the single energy spectrum x-ray dataset;
    decomposing the single energy spectrum x-ray dataset into a linear combination of energy dependence function, $b_k(\varepsilon)$, and corresponding expansion coefficients, $a_k(\vec{x})$;
    wherein $\vec{x}$ is a selected spatial location in the single energy spectrum x-ray dataset, $\varepsilon$ is an x-ray energy in the single energy spectrum x-ray dataset at the selected spatial location, and, k=1, 2, ..., K, to an index that labels material basis that is selected for decomposition;
    wherein $a_k(\vec{x})=\Sigma_j a_{k,j} e_j(\vec{x})$, $e_j(\vec{x})$ is an expanded image voxel basis function, where $j \in [1,N]$ and $N=N_x N_y N_z$ is a total number of image voxels in an image formed from the single energy spectrum x-ray dataset.

11. The method of claim 10 wherein decomposing the single energy spectrum x-ray dataset includes subjecting the single energy spectrum x-ray dataset to a multi-module system.

12. The method of claim 11 wherein the multi-module system includes:
    a material basis generator configured to decompose the single energy spectrum x-ray dataset into at least two material basis images;
    an en-chroma generator configured to regularize the material basis generator by enforcing an effective energy constraint; and
    a sinogram generator configured to generate projection data from the at least two material basis images.

13. The method of claim 10 further comprising receiving a user-selection of a desired energy for decomposition and wherein the decomposing is performed using the desired energy for decomposition.

14. A method for performing a material decomposition of a single energy spectrum x-ray dataset, the method comprising:
    accessing the single energy spectrum x-ray dataset;
    receiving a user-selection of a desired energy for decomposition; and
    decomposing the single energy spectrum x-ray dataset into a linear combination of energy dependence function using the desired energy for decomposition.

15. The method of claim 14 further comprising generating a set of images specific to the desired energy for decomposition from the single energy spectrum x-ray dataset.

16. The method of claim 14 wherein decomposing includes decomposing into a linear combination of energy dependence function, $b_k(\varepsilon)$, and corresponding expansion coefficients, $a_k(\vec{x})$, wherein $\vec{x}$ is a selected spatial location in the single energy spectrum x-ray dataset, $\varepsilon$ is an x-ray energy in the single energy spectrum x-ray dataset at the selected spatial location, and k=1, 2, ..., K, to an index that labels material basis that is selected for decomposition, and wherein $a_k(\vec{x}) = \Sigma_j a_{k,j} e_j(\vec{x})$, $e_j(\vec{x})$ is an expanded image voxel basis function, where $j \in [1,N]$ and $N=N_x N_y N_z$ is a total number of image voxels in an image formed from the single energy spectrum x-ray dataset.

17. The method of claim 14 wherein decomposing the single energy spectrum x-ray dataset includes subjecting the single energy spectrum x-ray dataset to a multi-module system.

18. The method of claim 17 wherein the multi-module system includes:
a material basis generator configured to decompose the single energy spectrum x-ray dataset into at least two material basis images;
an en-chroma generator configured to regularize the material basis generator by enforcing an effective energy constraint; and
a sinogram generator configured to generate projection data from the at least two material basis images.

19. The method of claim 18 wherein the material basis generator is configured to extract energy dependent linear attenuation coefficients for each image object in the single energy spectrum x-ray dataset to decompose the single energy spectrum x-ray dataset as a linear combination of energy dependence function $b_k(\varepsilon)$, and corresponding expansion coefficients $a_k(\vec{x})$, wherein $\vec{x}$ is a selected spatial location, $\varepsilon$ is an x-ray energy in the single energy spectrum x-ray dataset at the selected spatial location, and k=1, 2, ..., K, to serve as an index that labels material basis that is selected for decomposition.

20. The method of claim 19 wherein the material basis generator is configured to generate material basis images $a_k(\vec{x})$ from the single energy spectrum x-ray dataset.

21. The method of claim 20 wherein the output of material basis generator is configured to generate energy-resolved spectral CT images, as follows:

$$\mu(\vec{x},\varepsilon) = \Sigma_k a_k(\vec{x}) b_k(\varepsilon).$$

22. A medical imaging system comprising:
an x-ray source configured to deliver x-rays to an imaging patient at a single, selected x-ray energy spectrum;
a controller configured to control the x-ray source to acquire a single energy spectrum x-ray dataset from the imaging patient at the single, selected x-ray energy spectrum;
a material decomposition image reconstruction system comprising:
a material basis generator configured to decompose the single energy spectrum x-ray dataset into at least two material basis images;
an en-chroma generator configured to regularize the material basis generator by enforcing an effective energy constraint; and
a sinogram generator configured to generate projection data from the at least two material basis images.

23. The system of claim 22 wherein the en-chroma generator is configured to extract the effective energy from each datum in the single energy spectrum x-ray dataset, including the at least two material basis images.

24. The system of claim 22 wherein the material basis generator is configured to extract energy dependent linear attenuation coefficients for each image object in the single energy spectrum x-ray dataset to decompose the single energy spectrum x-ray dataset as a linear combination of energy dependence function $b_k(\varepsilon)$, and corresponding expansion coefficients $a_k(\vec{x})$, wherein $(\vec{x})$ is a selected spatial location, $\varepsilon$ is an x-ray energy in the single energy spectrum x-ray dataset at the selected spatial location, and k=1, 2, ..., K, to serve as an index that labels material basis that is selected for decomposition.

25. The system of claim 24 wherein the material basis generator is configured to generate material basis images $a_k(\vec{x})$ from the single energy spectrum x-ray dataset.

26. The system of claim 25 wherein the output of material basis generator is configured to generate energy-resolved spectral CT images, as follows:

$$\mu(\vec{x},\varepsilon) = \Sigma_k a_k(\vec{x}) b_k(\varepsilon).$$

27. The system of claim 26 wherein the energy dependence functions $b_k(\varepsilon)$ are specified by the materials used in material basis generator.

28. The system of claim 22 wherein at least one of the material basis generator or the en-chroma generator are formed of a learning network.

* * * * *